United States Patent [19]

Thome et al.

[11] Patent Number: 5,043,487
[45] Date of Patent: Aug. 27, 1991

[54] PREPARATION OF OCTADIENOLS

[75] Inventors: Alfred Thome, Ludwigshafen; Werner Bertleff, Viernheim, both of Fed. Rep. of Germany

[73] Assignee: BASF Aktiengesellschaft, Ludwigshafen, Fed. Rep. of Germany

[21] Appl. No.: 547,813

[22] Filed: Jul. 2, 1990

[30] Foreign Application Priority Data

Jul. 29, 1989 [DE] Fed. Rep. of Germany ....... 3925217

[51] Int. Cl.$^5$ .................. C07C 29/36; C07C 33/02
[52] U.S. Cl. ................................................ 568/909.5
[58] Field of Search ..................................... 568/909.5

[56] References Cited

U.S. PATENT DOCUMENTS

| | | | |
|---|---|---|---|
| 3,407,224 | 10/1968 | Smutny | 568/909.5 |
| 3,670,032 | 6/1972 | Romanelli | 568/909.5 |
| 3,992,456 | 11/1976 | Atkins et al. | 260/632 R |
| 4,417,079 | 11/1983 | Yoshimura et al. | 568/909.5 |
| 4,962,243 | 10/1990 | Roeper et al. | 568/909.5 |

FOREIGN PATENT DOCUMENTS 1354507 5/1974 United Kingdom ............. 568/909.5

Primary Examiner—J. E. Evans
Attorney, Agent, or Firm—John H. Shurtleff

[57] ABSTRACT

Octadienols are prepared by reacting 1,3-butadiene with water in the presence of a catalyst system comprising a palladium compound, a triorganophosphorus compound and carbon dioxide and in the additional presence of a triorganophosphine oxide.

7 Claims, 1 Drawing Sheet

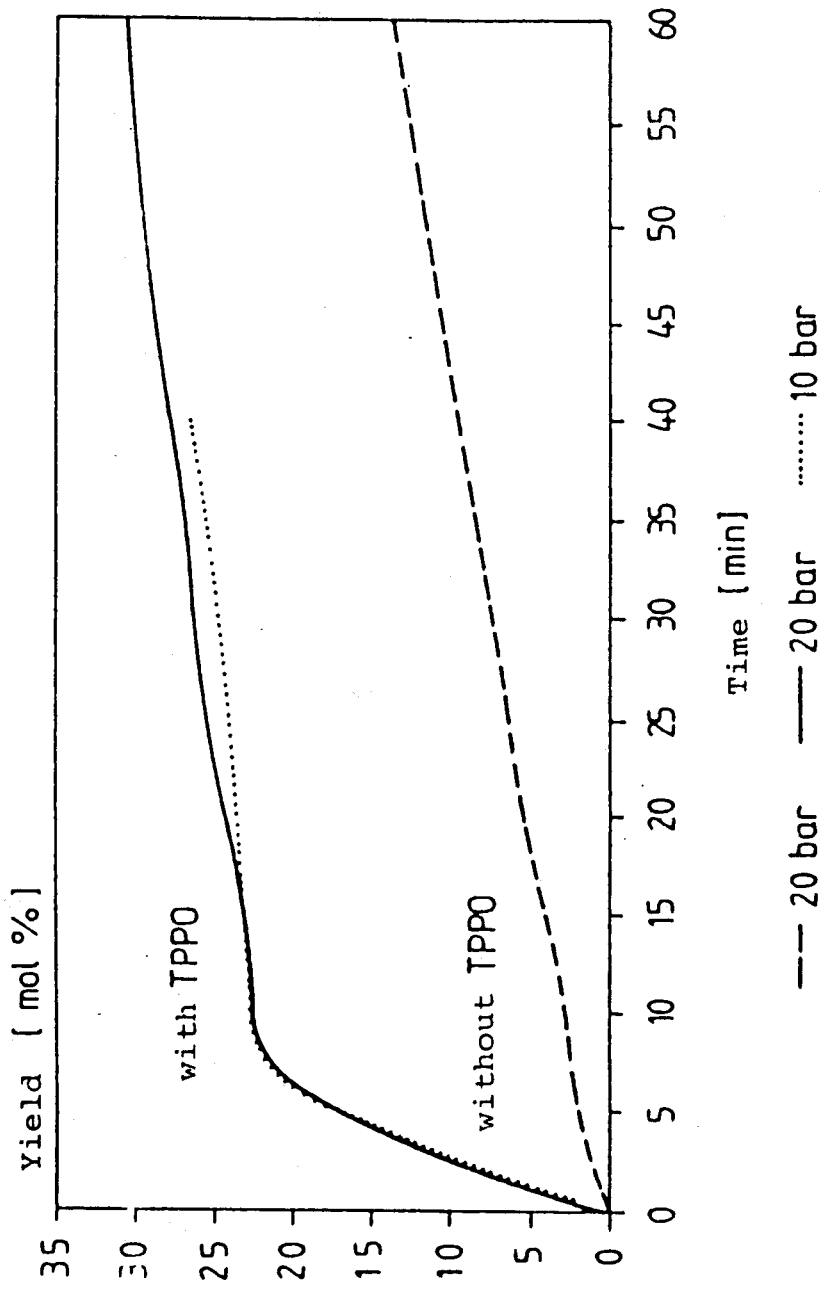

PREPARATION OF OCTADIENOLS

The present invention relates to an improved process for preparing octadienols by reacting 1,3-butadiene with water in the presence of a catalyst system comprising a palladium compound, a triorganophosphorus compound and carbon dioxide and in the additional presence of a triorganophosphine oxide.

Octadienols are usable inter alia as intermediates for preparing octyl alcohols which in turn find use in the preparation of plasticizers such as dioctyl phthalate. Since 1-octanol is preferred for this purpose, the most important octadienols are those which, like octa-2,7-dien-1-ol, are convertible into 1-octanol, but it is precisely these octadienols which have hitherto only been available in inadequate yields.

DE-A-20 18 054 discloses that the telomerization of butadiene with water in the presence of carbon dioxide, a solvent and a catalyst system formed from a palladium(0) or -(II) compound and a tertiary phosphine or phosphite produces octadienols

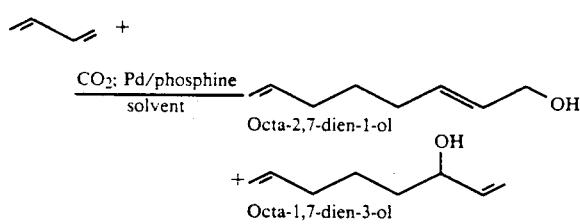

together with octadienyl ether and polyenes such as octa-1,3,7-triene as by-products.

However, the yields obtainable in respect of octadienols and the selectivity in respect of octa-2,7-dien-1-ol are unsatisfactory.

EP-A-330,999 describes a continuous process in which, to improve the reactivity and selectivity, a strong non-coordinating acid such as tetrafluoroboric acid, hexafluorophosphoric acid or trifluoromethanesulfonic acid is added to the reaction mixture comprising butadiene, water, carbon dioxide, palladium catalyst, phosphine ligands and inert solvent.

Nevertheless, the space-time yield of this reaction and hence the reaction rate leave something to be desired.

It is an object of the present invention to remedy the disadvantages described and to make in particular 2,7-octadien-1-ol obtainable in higher space-time yields than before.

We have found that this object is achieved by an improved process for preparing an octadienol by reacting 1,3-butadiene with water in the presence of a catalyst system comprising a palladium compound, a triorganophosphorus compound and carbon dioxide by performing the reaction in the additional presence of a triorganophosphine oxide.

The triorganophosphine oxide may be added to the system as phosphine oxide or may be formed wholly or in part in the reaction solution by adding an oxidizing agent, for example atmospheric oxygen, to convert the triorganophosphine ligand into the corresponding phosphine oxide.

Suitable organophosphine oxide compounds are basically all lipophilic and hydrophilic phosphine oxides. The amount of organophosphine oxide is not critical. Its molar ratio to palladium is preferably from 0.1:1 to 100:1, particularly preferably from 0.5:1 to 10:1. In general, the triorganophosphine oxide compounds used are triarylphosphine, diarylalkylphosphine, aryldialkylphosphine and trialkylphosphine oxides. Specific examples are: tributylphosphine oxide, dimethyl-n-octylphosphine oxide, tricyclohexylphosphine oxide, triphenylphosphine oxide, tritolylphosphine oxide, tris(p-methoxyphenyl)phosphine oxide, diphenylethylphosphine oxide and dimethylphenylphosphine oxide. Trialkylphosphine oxides are in general less suitable. Particularly preferred organophosphine oxides are not least for commercial reasons triarylphosphine oxides such as triphenylphosphine and tritolylphosphine oxides and arylalkylphosphine oxides such as diphenyl-$C_1$-$C_8$-alkylphosphine oxides. For commercial reasons it is further advisable to use the oxide of the triorganophosphine used.

To prepare the catalyst system, it is basically possible to use any soluble palladium (0) and palladium (II) compounds. Halogen-containing complexes and salts are less suitable. Suitable palladium (II) compounds are for example:
$Pd(OAc)_2$,
$Pd(dba)$ (dba = dibenzylideneacetone),
$[Pd(acac)(PPh_3)_2]BF_4$ (acac = acetylacetone),
$\partial Pd(h^3-C_3H_5(COD)]BF_4$ (COD = 1,5-cyclooctadiene)
and $[Pd(acac)(COD)]BF_4$
and primarily palladium (II) acetylacetonate. Suitable palladium (0) compounds are for example: tetrakis(triphenylphosphine)palladium tetrakis(dimethylphenylphosphine)palladium tetrakis(tris-p-methoxyphosphine)palladium bis(triphenylphosphine)($h^2$-ethylene)-palladium.

The amount of palladium compound is not critical, but is preferably from $10^{-5}$ to $10^{-1}$, in particular from $10^{-4}$ to $10^{-2}$, mol of palladium per mole of butadiene. The amount only affects the rate of reaction and thus is limited only by commercial factors.

The tertiary phosphorus compounds act as stabilizing ligands L in the active palladium complexes of the type

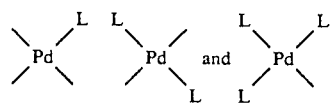

Suitable ligands L are basically all phosphines and phosphites, for example trialkyl- and triarylphosphines and trialkyl and triaryl phosphites having in total up to about 24 carbon atoms in the hydrocarbon moieties. Specific examples are: tributylphosphine, dimethyl-n-octylphosphine, tricyclohexylphosphine, tritolylphosphine, tris(p-methoxyphenyl)phosphine, diphenylethylphosphine, dimethylphenylphosphine, 1,2-bis-diphenylphosphinoethane, triethyl phosphite, tricyclohexyl phosphite and triphenylphosphite. It is also possible to use hydrophilic arylphosphines, preferably water-soluble salts of mono-, di- or trisulfonated triphenylphosphine compounds. Particular preference, not least for economic reasons, is given to triphenylphosphine. In general, the phosphines are preferred to the phosphites since the latter may undergo hydrolysis and rearrangement reactions. It is advantageous, but not absolutely necessary, to add that phosphine which corresponds to the triorganophosphine oxide added according to the present invention.

The amount of these ligands is in general from 1 to 20, preferably from 1 to 5, mol per mole of palladium.

The amount of carbon dioxide which promotes the butadiene telomerization in an as yet unknown manner is likewise not critical and may range from about $10^{-3}$ to 1, preferably from $10^{-2}$ to 0.5, mol per mole of butadiene.

Complete conversion of the butadiene into octadienols requires at least equimolar amounts of water (ie. a molar ratio of water to butadiene of 0.5:1), but it is advisable to employ a higher molar ratio of water to butadiene of up to about 10:1, preferably 5:1, in order to suppress the competing reactions leading to the formation of octadienyl ethers, octatriene and higher polyenes.

Suitable aprotic polar solvents are in particular ethers, since they are inert under the reaction conditions and show adequate or better solvent power not only from butadiene but also for water. Specific examples are diethyl ether, tetrahydrofuran and 1,4-dioxane.

Technically, it is particularly advantageous to employ those solvents which have a higher boiling point than the octadienols formed, since the octadienols can then simply be removed from the catalyst-containing solvent by distillation. Suitable high-boiling solvents are in particular polyalkylene glycol ethers of the formula

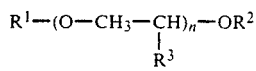

where $R^1$ and $R^2$ are each $C_1$–$C_3$-alkyl, $R^3$ is hydrogen or methyl, and n is from 2 to 6, preferably 4.

Other suitable high-boiling solvents are dialkyl sulfoxides such as, in particular, dimethyl sulfoxide and sulfones such as tetrahydrothiophene 1,1-dioxide (sulfolane).

Using a high-boiling solvent it is possible to good effect to carry out the process according to the present invention as a continuous process by reacting the abovementioned components with one another in a reaction vessel, transferring the reaction mixture to a distillation apparatus, and recycling unconverted butadiene and the catalyst-containing bottom product into the reaction vessel.

If desired, it is also possible to use noncoordinating strong acids. They include in particular tetrafluoroboric acid, hexafluorophosphoric acid, methanesulfonic acid, trifluoromethanesulfonic acid, sulfuric acid, trifluoroacetic acid, trichloroacetic acid and p-toluenesulfonic acid. Similarly, fatty acids are non-coordinating, so that it is also possible to use, for example, acetic acid, which in the present context still counts as a strong acid. However, acids which are weaker than acetic acid will in general not be used, since the effect of the acid generally decreases with decreasing strength.

Non-coordinating acids for the purposes of the present invention are those whose anions do not form stable complexes with transition metal cations such as palladium. Details concerning the theory of noncoordinating acids are given in the textbook by F. A. Cotton and G. Wilkinson, Anorganische Chemie, 3rd Edition, Verlag Chemie, Interscience Publishers, pages 179, 238, 394 and 506.

The ratio of acid to palladium is in general from 0.1 to 150, preferably from 50 to 100, equivalent % per mole of palladium.

The reaction is preferably carried out at from 50° to 70° C. Below 50° C, in particular below 30° C, the reaction slows down too much, and above 90° C, in particular above 100° C, undesirable secondary reactions occur which, however, may be thought acceptable if high space-time yields are considered more important.

As regards the pressure, it is advisable to employ the autogeneous pressure at the chosen reaction temperatures; said pressure will usually be within the range from 5 to 50, in particular from 10 to 30, bar.

An economically very advantageous embodiment of the process according to the present invention consists in the use of $C_4$-cuts instead of pure butadiene. The olefins 1-butene, 2-butene and isobutene present in the $C_4$-cut besides butadiene neither participate in nor impair the reaction. The $C_4$-cuts contain about 45% by weight of butadiene, 17% by weight of 1-butene, 10% by weight of 2-butene and 25% by weight of isobutene, the remainder being butane and isobutane.

The same is true of the workup of the reaction mixture. The reaction mixture is transferred from the reactor into a distillation apparatus, where unconverted 1,3-butadiene and octadienols are separated off by fractional distillation. The butadiene and the catalyst-containing bottom product are then recycled into the reaction vessel.

EXAMPLES

EXAMPLE 1 and COMPARATIVE EXAMPLE 1

In a 300-ml autoclave containing argon as protective gas, 0.22 g (0.72 mmol) of palladium acetylacetonate, triphenylphosphine (amount see Table 1) and triphenylphosphine oxide (amount see Table 1) were dissolved in 120 g (0.54 mol) of tetraglyme, and 0.03 g (0.34 mol) of tetrafluorohydroboric acid in 30 g (1.67 mol) of water was added. The autoclave was sealed, and 23.4 g (0.43 mol) of 1,3-butadiene and 4.4 g (0.1 mol) of carbon dioxide were injected via pressure lines. The mixture was then stirred at 60° C for 3 h. At the end of the run, the reactor was brought to room temperature and depressurized. The slightly yellow single-phase liquid discharge from the reactor was analyzed by gas chromatography. The internal standard used was n-octanol.

TABLE 1

| | Telomerization of butadiene in an autoclave | | | | | |
|---|---|---|---|---|---|---|
| | | | Yield [mol %] | | | |
| Run no. | TPP[a] [g] | TPPO[b] [g] | 2,7-od-1-ol[c] | 1,7-od-3-ol[d] | Total | n- content [%] |
| Comp. Ex. 1 | 0.56 | 0 | 59.8 | 5.2 | 65.0 | 92.0 |
| Ex. 1 | 0.56 | 0.59 | 64.2 | 4.7 | 68.9 | 93.2 |

[a] triphenylphosphine
[b] triphenylphosphine oxide
[c] 2,7-octadien-1-ol
[d] 1,7-octadien-3-ol As a comparison of the two runs the addition of triphenylphosphine oxide according to the present invention, equimolar to triphenylphosphine and in a molar ratio of 3:1 to palladium, increases the yield of 2,7-octadien-1-ol.

EXAMPLES 2 and 3 and COMPARATIVE EXAMPLE 2

200 g (3.7 mol) of 1,3-butadiene were pumped into a 2.5-1 piston-type stirred autoclave containing a mixture of 1,133 g (5.1 mol) of tetraglyme, 1.58 g (6.5 mmol) of palladium(II) acetylacetonate, triphenylphosphine (amount see Table 2), triphenylphosphine oxide (amount see Table 2) and 270 g (15 mol) of water under argon, and the reaction solution was heated to 60° C. Finally, the cocatalyst carbon dioxide was injected to the desired final pressure of 10 or 20 bar.

A sampling facility on the reactor made it possible to take several small samples per run at short time intervals.

The results of the runs at different $CO_2$ pressures are shown in graph form in the Figure and listed in Table 2 together with a comparative example.

TABLE 2

| Time [min] | Butadiene telomerization with water | | |
|---|---|---|---|
| | Yield[2] | | [mol %] |
| | Example 2[b] | Example 3[c] | Comparative Example 2[d] |
| 5 | 22.0 | 21.8 | 2.4 |
| 10 | 22.8 | 23.2 | 2.5 |
| 20 | 24.4 | 23.4 | 5.8 |
| 40 | 27.3 | 26.5 | 9.8 |
| 60 | 30.6 | | 13.8 |

[a]Total yield: 2,7-octadien-1-ol and 1,7-octadien-3-ol
[b]Pressure: 20 bar; 3.36 g (12.8 mmol) of triphenylphosphine and 1.78 g (6.4 mmol) of triphenylphosphine oxide
[c]Pressure: 10 bar; 3.36 g (12.8 mmol) of triphenylphosphine and 1.78 g (6.4 mmol) of triphenylphosphine oxide
[d]Pressure: 20 bar; 3.04 g (19.2 mmol) of triphenylphosphine The results show that the addition of triphenylphosphine oxide (molar ratio 1:2 relative to triphenylphosphine and 1:1 relative to palladium) leads to higher space-time yields of octadienols at various reaction pressures (10 and 20 bar). At a pressure of 20 bar triphenylphosphine oxide produces a total yield of 2,7-octadien-1-ol and 1,7-octadien-3-ol of 30.6 mol % in the course of 60 minutes compared with 13.8 mol % without added oxide, together with an n- content of 93.5% compared with 78.9%. The results of the run under 10 bar are similar to those under 20 bar.

We claim:

1. A process for preparing an octadienol by reacting 1,3-butadiene with water in the presence of a catalyst system comprising a palladium compound, a triorganophosphorus compound and carbon dioxide, which comprises performing the reaction in the presence of a triorganophosphine oxide.

2. A process as claimed in claim 1, wherein the molar ratio of triorganophosphine oxide to palladium is from 0.1:1 to 100:1.

3. A process as claimed in claim 2, wherein the molar ratio of triorganophosphine oxide to palladium is from 0.5:1 to 10:1.

4. A process as claimed in claim 2, wherein the molar ratio of water to butadiene is from 0.5:1 up to about 10:1.

5. A process as claimed in claim 1, wherein the reaction is carried out at a temperature of about 30° to 100° C.

6. A process as claimed in claim 2, wherein the reaction is carried out at a temperature of about 50° to 70° C.

7. A process as claimed in claim 1, wherein the reaction is carried out using, as a solvent for the water and butadiene, an inert aprotic organic solvent having a higher boiling point than the octadienol product.

* * * * *